US012408935B2

United States Patent
Storz et al.

(10) Patent No.: US 12,408,935 B2
(45) Date of Patent: *Sep. 9, 2025

(54) SHOCK WAVE DEVICE HAVING A SOURCE SELF ALIGNING WITH AN X-RAY DEVICE

(71) Applicant: Storz Medical AG, Tägerwilen (CH)

(72) Inventors: Rafael Storz, Tägerwilen (CH); Ernst Marlinghaus, Bottighofen (CH); Georg Görner, Landschlacht (CH); Arvid Kühl, Tägerwilen (CH); Felix Gremlich, Tägerwilen (CH)

(73) Assignee: STORZ MEDICAL AG, Tägerwilen (CH)

( * ) Notice: Subject to any disclaimer, the term of this patent is extended or adjusted under 35 U.S.C. 154(b) by 112 days.

This patent is subject to a terminal disclaimer.

(21) Appl. No.: 18/107,232

(22) Filed: Feb. 8, 2023

(65) Prior Publication Data

US 2023/0248382 A1 Aug. 10, 2023

(30) Foreign Application Priority Data

| Feb. 9, 2022 | (EP) | 22155802 |
| Feb. 9, 2022 | (EP) | 22155806 |
| Feb. 9, 2022 | (EP) | 22155808 |
| Feb. 9, 2022 | (EP) | 22155812 |

(51) Int. Cl.
*A61B 17/225* (2006.01)

(52) U.S. Cl.
CPC ...... *A61B 17/2256* (2013.01); *A61B 17/2255* (2013.01)

(58) Field of Classification Search
CPC .................. A61B 17/2256; A61B 17/2255
See application file for complete search history.

(56) References Cited

U.S. PATENT DOCUMENTS

| 4,763,652 A | 8/1988 | Brisson et al. |
| 4,984,575 A | 1/1991 | Uchiyama et al. |
| 5,065,740 A | 11/1991 | Itoh |
| 6,041,500 A * | 3/2000 | Terpstra ................ B23P 15/006 29/889.22 |
| 6,048,750 A * | 4/2000 | Hembree .............. H01L 21/681 438/107 |
| 6,239,590 B1 * | 5/2001 | Krivy ................... G01R 35/005 324/750.02 |
| 2003/0106230 A1 * | 6/2003 | Hennessey ........... B25J 17/0216 33/645 |
| 2009/0275866 A1 | 11/2009 | Gelbart et al. |

(Continued)

FOREIGN PATENT DOCUMENTS

| DE | 3621935 A1 | 1/1988 |
| DE | 3943644 C2 | 11/1995 |

(Continued)

*Primary Examiner* — Bo Joseph Peng
(74) *Attorney, Agent, or Firm* — Quarles & Brady, LLP; Yakov Sidorin (57) ABSTRACT

A shock wave and/or ultrasound therapy system includes an ultra-sound and/or shockwave source suspended on a hexapod drive and an X-ray system. A system controller configured to generate control signals for the hexapod drive to align the ultrasound and/or shockwave source with the X-ray system based on the displacement of a known object between two images taken at different tilt angles of the X-ray system.

10 Claims, 10 Drawing Sheets

(56) References Cited

U.S. PATENT DOCUMENTS

| | | | |
|---|---|---|---|
| 2010/0080349 | A1 | 4/2010 | Kalender et al. |
| 2011/0006943 | A1* | 1/2011 | Shaffer ................. G01S 17/933 342/146 |
| 2013/0085531 | A1* | 4/2013 | Hartman ................. A61H 1/02 606/245 |
| 2016/0031080 | A1* | 2/2016 | Rey ..................... B25J 19/0091 901/22 |
| 2016/0114194 | A1 | 4/2016 | Gertner |
| 2019/0350685 | A1 | 11/2019 | Saghatchi et al. |

FOREIGN PATENT DOCUMENTS

| | | |
|---|---|---|
| DE | 10260594 A1 | 7/2004 |
| DE | 102005039178 A1 | 3/2007 |
| DE | 102010061852 A1 | 5/2012 |
| EP | 1506741 A1 | 2/2005 |
| EP | 2340781 A1 | 7/2011 |
| EP | 2628456 A1 | 8/2013 |
| EP | 3875048 A1 | 9/2021 |
| WO | 2008048708 A2 | 4/2008 |

\* cited by examiner

SHOCK WAVE DEVICE HAVING A SOURCE SELF ALIGNING WITH AN X-RAY DEVICE

CROSS-REFERENCE TO RELATED APPLICATIONS

This application claims priority from and benefit of the pending European Application No. 22155806.7 filed on Feb. 9, 2022, European Application No. 22155802.6 filed on Feb. 9, 2022, European Application No. 22155808.3 filed on Feb. 9, 2022 and European Application No. 22155812.5 filed on Feb. 9, 2022. The disclosure of each of these patent documents is incorporated by reference herein.

BACKGROUND

1. Field of the Invention

The invention relates to an extracorporeal shock wave or ultrasound therapy system, e.g., a lithotripsy system or Lithotripter for non-invasive treatment of stones, like e.g., kidney stones, urinary stones, gallstones, or other calculi within a mammal's body using acoustic pulses, or other applications of an extra-corporeal shock wave or ultrasound therapy system.

2. Description of Related Art

In a lithotripsy system, X-ray images are taken from a patient. These images are used for locating a stone and for aligning a therapy source like a shock wave or ultrasound therapy source. Such an X-ray image shows a projection into a plane orthogonal to the X-ray beam, herein referred ax X-Y plane. An information about the height, herein the Z-axis is not available. When the X-ray source is rotated about a predetermined angle alpha about a rotation axis parallel to the X-Y plane, all points at the rotation axis remain at their positions.

In view of this, the lithotripsy system is calibrated such that the focal area of the therapy source is at the rotation axis. This is done by taking at least two X-ray images under different angles alpha1 and alpha2 and comparing the positions of an object, e.g., stone or calibration object in the X-ray images. If the position differs, the object is not at the rotation axis. Normally, the X-ray system is moved to bring the object into the rotation axis.

EP 150 674 1 A1 discloses a lithotripsy system where the X-ray system can be mechanically coupled to the shockwave source for alignment. The axis of the x-ray system should be parallel to the axis of the shockwave source, further the focal area of the shockwave source should be on the axis of the x-ray system. This allows for proper triangulation and targeting. Mechanically coupling is a straightforward approach which requires a complex mechanical system and prevents separating the X-ray device from the shockwave device.

EP 2 628 456 A1 discloses a shock wave therapy device with dynamic target tracking. US 2010/080349 A1 discloses a breast biopsy device. EP 3 875 048 A1 discloses a shockwave therapy system with 3D control. US 2019/0350685 A1 discloses an electromagnetic navigation system.

SUMMARY OF THE INVENTION

The embodiments are providing an ultrasound and/or shock wave device, including an ultrasound and/or shockwave source and an X-ray system wherein the ultrasound and/or shockwave source is automatically aligned with the X-ray system without mechanically coupling between the ultrasound and/or shockwave source without mechanically coupling. The shock waves may be propagating in a direction to a patient table.

A skilled person is well aware that the nature of the shock waves and that of ultrasound are substantially the same: both are acoustic waves, with certain distinctions manifesting mostly in corresponding pressure amplitudes as well as periodicity of oscillations associated with ultrasound waves (as opposed to the shock waves characterized by a single, mostly positive pressure pulse followed by a comparatively small tensile wave component, as discussed, for example, at storzmedical.com/us/physics-and-technology). Accordingly, the skilled artisan will readily appreciate the definitiveness and lack of ambiguity of the used herein terms such as, for example, ultrasound and/or shock wave source, which refers to and define a source configured to generate an acoustic wave in the form or either ultrasound, or in the form of a shock, or in a mix of ultrasound and a shock wave. Similar terms are defined in a similar fashion.

A further problem to be solved is to provide an ultrasound and/or shock wave device, which allows treatment of organs or areas within organs independent of respiration or other movements of the organ and/or patient. The ultrasound and/or shock wave device should be comparatively robust and simple to use.

Another problem to be solved is to provide an ultrasound and/or shock wave device, which can avoid and/or remove air bubbles at the exterior surface of a cushion of a lithotripsy device covering an ultrasound and/or shock-wave source. A further aspect relates to a method of removing remove air bubbles at the exterior surface of the cushion.

In an embodiment, a shock wave and/or ultrasound device, which may be a lithotripter includes an ultrasound and/or shockwave source together with an X-ray system including an X-ray source and a detector. It may further include a patient table. The ultrasound and/or shockwave source is suspended on a hexapod, such that it can be displaced in three degrees of freedom and tilted or rotated about two or three degrees of freedom. Therefore, no complex X-ray system mechanism and complex X-ray adjustment procedures are required. The X-ray system may only be aligned coarsely. The treatment source may then be adjusted by the hexapod drive such that the axes of the X-ray system and the treatment source are the same. As the hexapod allows a free orientation of the source in space, it can basically adjust the treatment source to any orientation of the X-ray source.

The X-Ray system, the ultrasound and/or shockwave source are oriented in a cartesian coordinate system as follows: a y-axis may be a longitudinal axis through the center of the table. An x-axis may be orthogonal to the y-axis and in the plane of the table surface. A z-axis is orthogonal to the plane of the table surface and therefore orthogonal to the x-axis and the y-axis and in a direction upward from the table. There may also be a first rotation around the x-axis, a second rotation and a third rotation around the z-axis. A positive rotation may be a clockwise rotation in a direction of a positive axis.

The orientation of the ultrasound and/or shockwave source is defined by an axis extending from the center of the source to the center of the focal area. The orientation of the X-ray system is defined by an axis at the path of the X-ray beam between the X-ray source and the detector.

The shock wave or ultrasound therapy system may include a system controller which may control at least the X-ray system and the hexapod drive of the ultrasound and/or shockwave source. The system controller may control the X-ray system for taking at least one X-ray image which may show a known object, which may be a calibration object or at least a part of the ultrasound and/or shockwave source. The known object may be a calibration phantom or focal phantom and may include a first X-ray absorbing object and a second X-ray absorbing object arranged distant from each other symmetrically to or at the axis of the ultrasound and/or shockwave source. Both X-ray absorbing objects may have different sizes and a symmetrical structure. They may be rings of different diameters. The known object may also be part of the structure of the shock wave and/or ultrasound therapy system, which may be visible in an X-ray image.

The system controller may be configured to control the X-ray system to take a first image showing a first X-ray absorbing object and a second X-ray absorbing object.

The system controller may be configured to process the first image, to detect the first and second X-ray absorbing objects and to estimate the displacement of axes between a center axis of the ultra-sound and/or shockwave source and a center axis of the X-ray system. This may be done based on calculating the centers of and/or the distance between the X-ray absorbing objects.

The system controller may further be configured to control the hexapod drive for moving of the ultrasound and/or shockwave source to compensate for the displacement of axes.

The system controller may further be configured to control the X-ray system to take a second image showing a first X-ray absorbing object and a second X-ray absorbing object.

The system controller may be configured to process the second image, to detect the first and second X-ray absorbing objects and to estimate the displacement of axes between a center axis of the ultrasound and/or shockwave source and a center axis of the X-ray system. The system controller may further be configured to control the hexapod drive for further adjustment if the displacement of axes is above a limit value. This may be repeated until the displacement of axes is below or equal to the limit value or a maximum count of iterations have been reached.

The system controller may be configured to take at least a further image after changing alignment of the ultrasound and/or shockwave source to verify the alignment. It may further be configured to repeat the steps above until an alignment within predetermined limits is reached or an operator is satisfied, or a maximum number of cycles is reached.

The ultrasound and/or shockwave source may be of any type suitable for generating strong ultrasound signals and/or shock waves. Depending on the specifics of a particular implementation, such source may include a shock wave generator and/or transducer, which may include at least one of a coil, a spark gap or a Piezo transducer. The shock wave generator/transducer may be partially enclosed by a reflector. Depending on the type of transducer, the reflector may have a parabolic or half-elliptic shape. In case of a piezo transducer, the transducer may itself have a spherical shape, such that a reflector may not be needed. The ultrasound and/or shockwave source may have a focal volume which is distant from the ultrasound and/or shockwave source and normally around a center axis of the ultrasound and/or shockwave source. The focal volume may be defined as a volume, where the maximum shock wave intensity is maintained with a deviation of maximal −3 dB or −6 dB. If the focal volume is defined with a 6 dB deviation, the pressure at the limit of the zone is half of the maximum pressure inside the zone. The focal volume may have an elliptical shape with a length in an axial direction (defined by the center axis) of the ultrasound and/or shockwave source axis of 10 to 15 cm and a diameter between 5 and 15 mm. The focal volume normally is spaced from the shock wave generator and/or transducer.

The hexapod drive bearing the ultrasound and/or shockwave source is also known as a hexapod platform. Such a hexapod platform also is called a Stewart platform. Basically, it is a type of parallel manipulator or parallel robot that has six linear actuators, which may be hydraulic or pneumatic jacks or electric linear actuators. Examples of electric linear actors are motors coupled to a belt or a spindle to perform a linear movement. These linear actuators are connected in pairs to three mounting positions at a base, crossing over to three mounting positions at the ultrasound and/or shockwave source. Each connection of a linear actuator to either the base or the ultrasound and/or shockwave source may include a universal joint, also called a cardan joint or a ball joint. By variation of the length of the linear actuators, the ultrasound and/or shockwave source can be moved in six degrees of freedom with respect to the base. There are three degrees of translation and three degrees of rotation. In alternative to six linear actuators, a lower number of actuators may be provided, e.g., like in a delta robot with three actuators.

The ultrasound and/or shockwave source may be mounted below the patient table. In general, a shockwave source may be mounted in alternative ways, e.g., on a stand or support.

Due to movements of a patient's body, e.g., by respiration or heartbeat, an object to be treated may move out of the focal volume. For example, a movement of the chest causes a movement of the kidneys in a cranio-caudal direction, which is approximately parallel to the surface of the patient table accommodating the patient. The amplitude of displacement of the kidneys normally is in the range of 20 to 40 mm. As the center axis of a normal shock wave generator is approximately orthogonal to the surface of the patient table, a kidney stone may easily move out of the focal volume. The respiration frequency of an anesthetized person may be in the range of 0.3 to 0.5 Hz.

The hexapod drive allows to adjust the position of an ultrasound and/or shockwave source relative to a patient's body and/or the X-ray system. Positioning of the ultrasound and/or shockwave source may be done automatically or by manual control. An automatic control may allow quick adjustment and it may also allow to store and retrieve preconfigured settings.

Such a hexapod drive is a very robust and mechanical stiff support or suspension of the ultrasound and/or shockwave source. Therefore, it can withstand high forces from the patient body, the weight of the ultrasound and/or shockwave source and dynamic loads which occur when shockwave pulses are generated. Further, a hexapod drive can be moved quickly. Therefore, a stable positioning of the ultrasound and/or shockwave source is achieved providing the additional ability to quickly correct deviations and movements by the patient.

A hexapod drive may allow movement in all 6 degrees of freedom. This allows for a precise adjustment of the position of the focal volume of the ultrasound and/or shockwave source and/or the path of the ultrasound and/or shockwave though the body of the patient.

The patient table may have a basically planar surface defining a longitudinal axis. It is configured for accommodating a patient. The ultrasound and/or shockwave source may be mounted below the patient table. In general, a shockwave source may be mounted in alternative ways, e.g., on a stand or support.

The base may be standing on a floor directly or by a stand or it may be attached to a floor. The base may also hold the table.

The patient table may be positioned for a slow and coarse adjustment in 3 degrees of translation for larger distances whereas the hexapod drive provides a comparatively quick adjustment in 3 degrees of translation and 3 degrees of rotation. The movement distances of the table may be larger than the movement distances of the hexapod drive.

A method of aligning an ultrasound and/or shockwave source with an X-ray system includes the steps of:
  a) taking a first image with the X-ray system at a first position of the X-ray system relative to the ultrasound and/or shockwave source, the image showing a first X-ray absorbing object and a second X-ray absorbing object arranged distant from each other at the axis of the ultrasound and/or shockwave source,
  b) using the first image, calculating the centers of and/or the distance between the first X-ray absorbing object and the second X-ray absorbing object, and estimating the displacement of axes between a center axis of the ultrasound and/or shockwave source and a center axis of the X-ray system by a system controller,
  c) moving of the ultrasound and/or shockwave source by means of a hexapod drive to compensate for the displacement of axes,
  d) taking a second image with the X-ray system at a second position of the X-ray system, the image showing a first X-ray absorbing object and a second X-ray absorbing object,
  e) using the second image, calculating the centers of and/or the distance between the first X-ray absorbing object and the second X-ray absorbing object, and estimating the displacement of axes between a center axis of the ultrasound and/or shockwave source and a center axis of the X-ray system by the system controller.
  f) repeating the sequence from step c) if displacement of axes is above a limit value.

If the axes are not aligned and the displacement of axes is above a limit value, the steps c), d) and e) may be repeated multiple times until the displacement of axes is below a limit value.

The X-ray system, the ultrasound and/or shockwave source are oriented in a cartesian coordinate system as defined above.

As the position of the focal volume moves in synchronicity with the kidney stone, generating of shock wave pulses at any time will result in a high energy coupling into the stone and a high treatment efficiency.

For heart treatment, respiration and heartbeat may be considered. This may require a tilting movement about two different axes with different frequencies. Basically, all parts of a body may be treated by compensating any movement by a tilting movement.

A fine adjustment of the amplitude of the tilting movement may either be made manually by a user who may watch the imaging system and an indication of the focal volume. Further, adjustment of the amplitude may be made automatically, for example by a computer system, analyzing the images of the imaging system.

A display may be provided indicating an image from an imaging system, like an x-ray image or and ultrasound image, which may further indicate the focal volume. Based on this, a user may estimate the quality of adjustment and treatment. Additional image analysis may provide a figure of merit as feedback for the user with graphical indicators (bar graphs, colored feedback etc.).

Due to the body movement or respiration tracking of the ultrasound and/or shockwave source, any shock wave repetition frequency, may be selected independent of the respiration frequency.

In an embodiment, the ultrasound and/or shockwave source may be rotated around the center axis about an angle in a range between +/−2° to +/−20°. The range may be between +/−5° and +/−15°. In a typical application, a range of +/−10° would meet most requirements. Usually, kidneys and kidney stones have a slightly outward movement in addition to the movement parallel to the patient table, which may be compensated by such a rotation around the center axis. In a very simple embodiment, there may be only two discrete angle settings, for example at +10° and at −10°, one for the left kidney and the other for the right kidney, which would suit most patients. In another embodiment, a larger number of positions may be provided.

The basic concept explained herein at the example of a kidney stone may also be applied to a urethra stone or other concrements in a body.

A method of focusing an ultrasound and/or shockwave source on a hexapod platform to a kidney stone includes the steps of:
  a) receiving a respiration signal indicative of a respiration,
  b) amplifying the signal and optionally adding an offset,
  c) tilting an ultrasound and/or shockwave source about an angle proportional to the signal.

The tilt axis may be an axis in a plane essentially parallel to a plane of a patient table and essentially orthogonal to a longitudinal axis of the patient table, including deviations in parallelism and/or orthogonality of +/−300.

The method may further include the steps of rotating the ultrasound and/or shockwave source around its center axis or a fixed angle before performing the steps a to c.

In an embodiment, a shock wave and/or ultrasound device, which may be a lithotripter may include an ultrasound and/or shockwave source within a reflector and covered by a cushion. The interior of the reflector and the cushion may be filled with a liquid, which may be water. The cushion may have an exit section through which ultrasound and/or shockwaves pass to the exterior. This exit section may be directly coupled to a patient or indirectly via a separation film, also called patient film to the patient. The patient film may include a plastic material. There may be a layer of coupling gel, also known as ultrasound gel or acoustic gel at the top of the exit section to allow further coupling of the ultrasound and/or shockwave energy via the patient film or directly to the patient.

In an embodiment, a shock wave and/or ultrasound device, which may be a lithotripter includes an ultrasound and/or shockwave source within a reflector and covered by a cushion. The interior of the reflector and the cushion may be filled with a liquid, which may be water. The cushion may have an exit section through which ultrasound and/or shockwaves pass to the exterior. This exit section may be directly coupled to a patient or indirectly via a separation film, also called patient film to the patient. The patient film may include a plastic material. There may be a layer of coupling gel, also known as ultrasound gel or acoustic gel at the top of the exit section to allow further coupling of the ultrasound and/or shockwave energy via the patient film or directly to the patient.

The ultrasound and/or shockwave source may be suspended on a hexapod drive, such that it can be displaced and tilted. Displacement may be in at least one and up to three degrees of freedom. Tilt or rotation may be in at least one and up to three degrees of freedom. As the hexapod drive allows a free orientation of the source in space, it can basically adjust the ultrasound and/or shockwave source to any required position and orientation.

The hexapod drive may be configured to move the ultrasound and/or shockwave source towards the patient until the exit section of the cushion touches the patient film or the patient. Such a movement may help to remove small bubbles of air within a coupling medium, e.g., an ultrasound gel or another immersion media, in the space between the top of the cushion and the patient and specifically air bubbles which may be between the top of the cushion and the patient film and/or between the patient film and the patient body. This movement may be done before an ultrasound and/or shockwave treatment is started. The hexapod drive may further be configured to perform additional lateral and/or rotational movements which may help further to wipe out or remove air bubbles from the coupling gel at the top of the exit section of the cushion. If, for example, the main movement direction is along the positive z-axis, the additional movement may be in the x-y-plane defined by the x-axis and y-axis. There may also be a rotation about the z-axis.

In an embodiment, the hexapod drive may be configured to perform at least one lateral and/or rotational movement. Such a movement may be relative to the center axis of the ultrasound and/or shockwave source. This movement may help to wipe out or remove air bubbles from the coupling gel at the top of the exit section of the cushion. If, for example, the center axis of the ultrasound and/or shockwave source is along the positive z-axis, the movement may be in the x-y-plane defined by the x-axis and y-axis. There may also be a rotation about the z-axis.

A slight off axis component of the lateral and/or rotational movement which may result in a wobble, may improve removal of bubbles.

Further, there may be movements in alternating directions, and even reversal of direction. Also, rotations and lateral displacements may be combined concurrently (at the same time) or alternating.

In an embodiment, a spiral movement in an X-Y plane may be combined with a translation in Z direction towards the patient. The movement may start centered close to the center axis making circles with continuously increasing radius and moving at the same time towards the patient. The movement may start with an axial offset to the center axis. The spiral may have only one or two turns. A higher number of turns is also possible. The X-Y plane may be a plane of the patient table and the Z direction may be orthogonal thereto.

The hexapod drive may be configured to provide a spiral movement in a plane orthogonal to the center axis of the ultrasound and/or shockwave source combined with a translation in a direction of the center axis. This translation may be in a direction to a patient film and/or a patient.

A patient film may be part of the patient table.

In an embodiment, a movement along the center axis of the ultrasound and/or shockwave source, in z-direction may be done with the ultrasound and/or shockwave source tilted slightly around an axis in the x-y-plane such that the top of the exit section of the cushion approaches the patient film or patient under an angle. When a first edge of the cushion touches or approaches the patient film or patient closer than a minimum distance, the ultrasound and/or shockwave source may be tilted, such, that it is parallel to the patient film or patient.

BRIEF DESCRIPTION OF THE DRAWINGS

In the following, the invention will be described by way of example, without limitation of the general inventive concept, on examples of embodiments and with reference to the drawings, of which.

Generally, the drawings are not to scale. Like elements and components are referred to by like labels and numerals. For the simplicity of illustrations, not all elements and components depicted and labeled in one drawing are necessarily labels in another drawing even if these elements and components appear in such other drawing.

While various modifications and alternative forms, of implementation of the idea of the invention are within the scope of the invention, specific embodiments thereof are shown by way of example in the drawings and are described below in detail. It should be understood, however, that the drawings and related detailed description are not intended to limit the implementation of the idea of the invention to the particular form disclosed in this application, but on the contrary, the intention is to cover all modifications, equivalents and alternatives falling within the spirit and scope of the present invention as defined by the appended claims.

DETAILED DESCRIPTION

Figure 1:
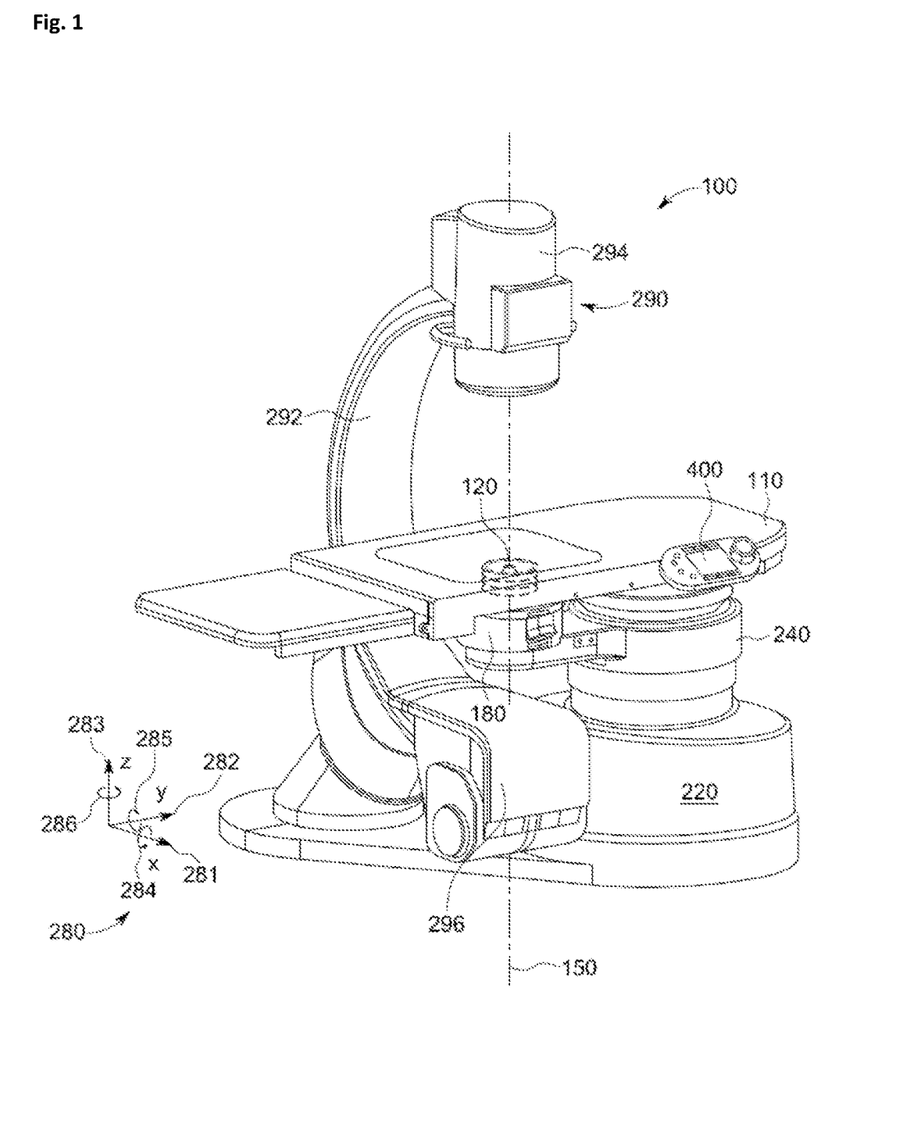
FIG. 1 shows an embodiment of a lithotripsy system.

In FIG. 1, a first embodiment of a lithotripsy system is shown. The embodiments may be implemented with any ultrasound and/or shockwave treatment system.

An extra-corporeal ultrasound and/or shockwave lithotripsy system for non-invasive treatment of stones 100 includes a patient table 110, an ultrasound and/or shockwave source 120. The ultrasound and/or shockwave source 120 is mounted to a hexapod drive 180. The hexapod drive 180 may further be held by a stand 220. The hexapod drive 180 allows fine positioning of the ultrasound and/or shockwave source 120 in multiple axes relative to the patient table 110 and therefore relative to the patient (not shown in this figure). The ultrasound and/or shockwave source 120 has a focal volume which moves together with the source. In an embodiment the distance of the focal volume to the source may be modified.

The patient table 110 is based on a stand 220 which may stand on a floor. The table 110 may be held by a positioning device 240 to move the table relative to the ultrasound and/or shockwave source 120 together with the hexapod drive 180. A movement of the patient table may be coarse positioning which may be limited to a displacement in 3 axes.

The table 110 may have a flat surface for accommodating a patient who is not shown here.

An X-ray device 290, acting as targeting device, may be provided. It may have an X-ray tube 296 opposing an X-ray detector 294, both mounted tiltable at a C-arm 292. There is a common center axis 150 on which the X-ray device and the ultrasound and/or shockwave source are aligned.

To describe the relative movement of the table 110, the X-ray device 290 and the ultrasound and/or shockwave source 120, a cartesian coordinate system 280 may be used. There is a y-axis 282, which may be a longitudinal axis through the center of the table. Furthermore, there is an x-axis 281 orthogonal to the y-axis and in the plane of the table surface. A z-axis 283 is orthogonal to the plane of the table surface and therefore orthogonal to the x-axis and the y-axis. There may also be a first rotation 284 around the x-axis, a second rotation 285 and a third rotation 286 around the z-axis. A positive rotation may be a clockwise rotation in a view along a positive axis.

A hexapod drive 180 may allow movement in all these 6 degrees of freedom. This allows for a precise adjustment of the position of the focal volume of the ultrasound and/or shockwave source 120. The patient table may be positioned for a slow and coarse adjustment in 3 degrees of translation for larger distances, but normally no rotation, whereas the hexapod drive provides a comparatively quick adjustment in 3 degrees of translation and 3 degrees of rotation. The movement distances of the table may be larger than the movement distances of the hexapod drive. The X-ray device may at least be tiltable to perform a second rotation 285 around an axis parallel to the y-axis 282. It may also be tiltable around an axis parallel to the Y axis. It may further be translated in a plane defined by the X and Y axis. This means, it may be moved on the floor which is also in the X-Y plane.

For control of the movement of the ultrasound and/or shockwave source 120 relative to the patient table 110, a control panel 400 may be provided.

Figure 2:
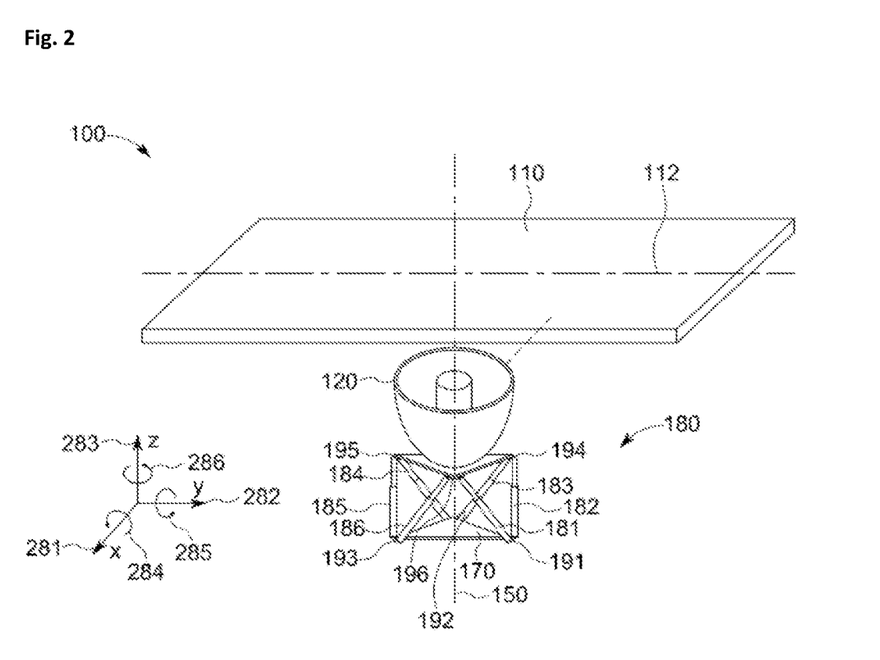
FIG. 2 shows a perspective view of an ultrasound and/or shockwave source mounted to a hexapod drive.

FIG. 2 shows a more schematic perspective view of an ultrasound and/or shockwave source 120 mounted to a hexapod drive 180. A shock wave or ultrasound device, which may be a lithotripter 100 may include a patient table 110 and an ultrasound and/or shockwave source 120. The ultrasound and/or shockwave source 120 may be arranged below the patient table 110, such that a patient (not shown here) may be accommodated on top of the patient table. The patient table may have a longitudinal axis 112. There may be a hole or cutout in the patient table at the position of the ultrasound and/or shockwave source.

The ultrasound and/or shockwave source 120 is supported by and/or suspended on a hexapod drive 180. Basically, it is a type of parallel manipulator or parallel robot that has six linear actuators 181-186, which may be hydraulic or pneumatic jacks or electric linear actuators. These linear actuators are connected in pairs to three mounting positions 191, 192, 193 at a base 170, crossing over to three mounting positions 194, 195, 196 at the ultrasound and/or shockwave source 120. Each connection of a linear actuator to either the base or the ultrasound and/or shockwave source may include a universal joint, also called a cardan joint or a ball joint. By variation of the length of the linear actuators, the ultrasound and/or shockwave source can be moved in six degrees of freedom with respect to the base. There are three degrees of translation, parallel to at least one X-axis 281, Y-axis 282, Z-axis 283 and three degrees of tilt or rotation including a first tilt 284 around an axis parallel to X-axis 281, a second tilt 285 around an axis parallel to Y-axis 282, a third tilt 285 around an axis parallel to Z-axis 283.

Further, the ultrasound and/or shockwave source 120 may have a center axis 150.

Figure 3:
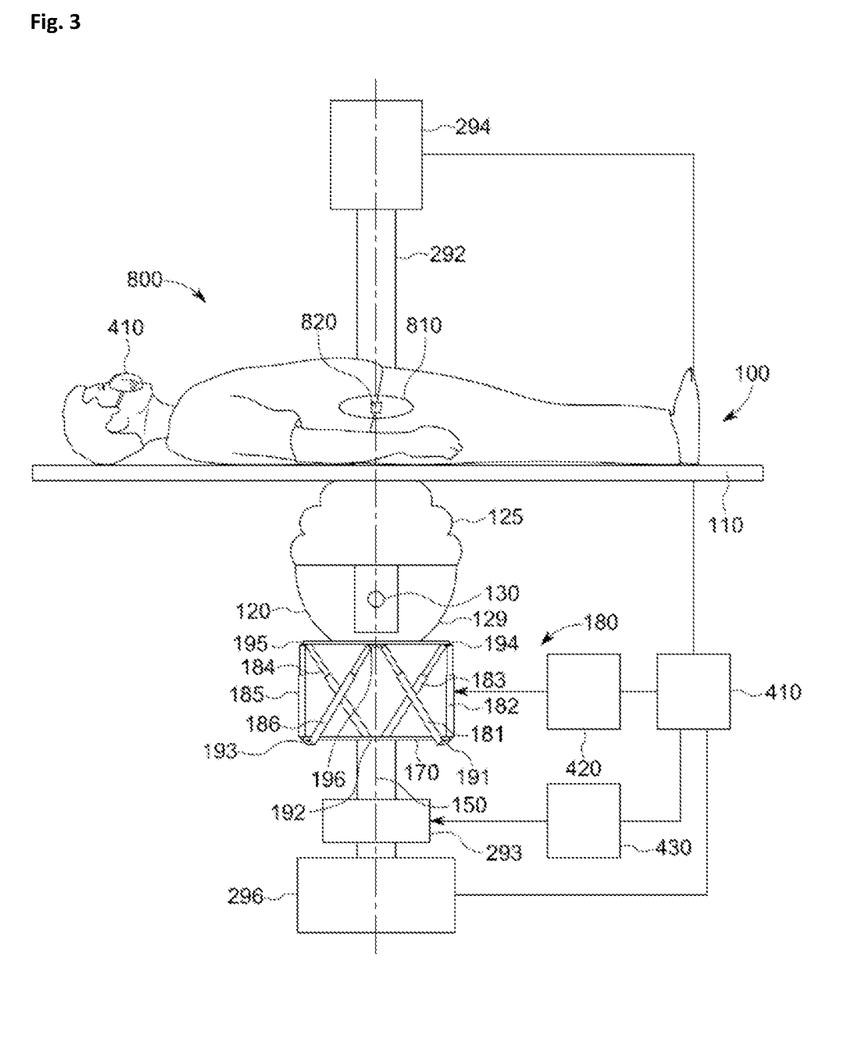
FIG. 3 shows an embodiment of a therapy system.

FIG. 3 shows an embodiment in a side view. In this figure, a patient 800 is positioned on top of the patient table 110. The patient may have a kidney 810 with a kidney stone 820. An X-ray system includes an X-ray tube 294 shown below the patient and an X-ray detector 294 shown above the patient, both connected and held by a C-arm 292. Here, the X-ray system is aligned with the shock wave generator 130 such that both are on the axis 150. The X-ray system may further include a C-arm drive 293, which may be an electrical motor with a gear.

A system controller controls at least operation of the X-ray system 290, of the C-arm by means a C-arm control 430 and of the hexapod drive 180 by means of a hexapod control 420. The system controller may also control the X-ray tube 296 and may receive images from the X-ray detector 294.

Below the table 110, the ultrasound and/or shockwave source 120 is shown in a sectional view. It may have a shock wave generator 130 which may be a coil as shown herein and which is at least partially enclosed by a reflector 129. Further, the center axis 150 is marked as a dashed line. Normally, the interior of the reflector and the space between the source and the patient is filled with a liquid like water or another shockwave conducting medium. To contain the water within the volume, a coupling cushion 125 may be provided.

Figure 4:
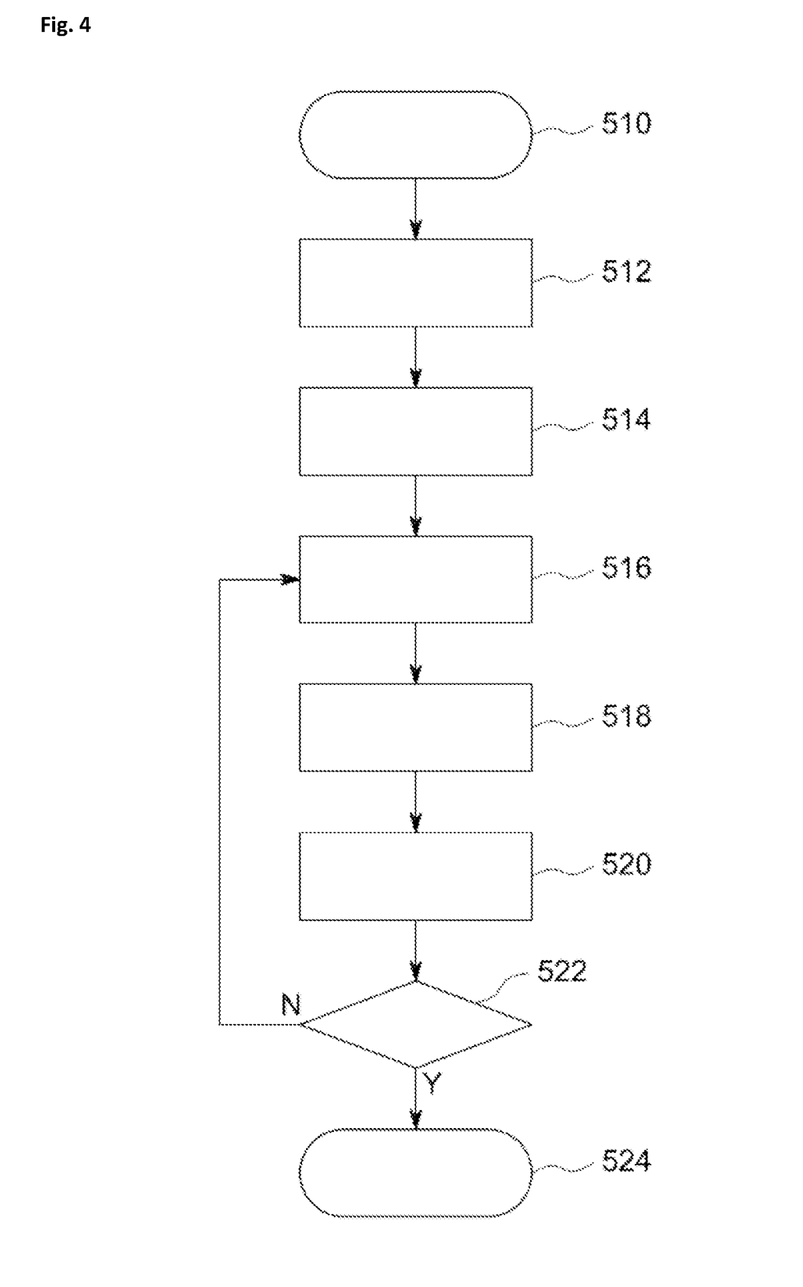
FIG. 4 shows a flow diagram of a method.

FIG. 4 shows a flow diagram of a method of aligning an ultrasound and/or shockwave source 120 with an X-ray system. The method utilizes a focal phantom including a first X-ray absorbing object 127 and a second X-ray absorbing object 128 arranged distant from each other at the axis of the ultrasound and/or shockwave source 120. The method including the steps of:

510: Start

512: taking a first image with the X-ray system at a first position of the X-ray system 290 relative to the ultrasound and/or shockwave source 120, the image showing a first X-ray absorbing object 127 and a second X-ray absorbing object 128 arranged distant from each other at the axis of the ultrasound and/or shockwave source 120,

514: processing of the first image, calculating the centers of and/or the distance between the first X-ray absorbing object 127 and the second X-ray absorbing object 128, and estimating the displacement of axes between a center axis of the ultrasound and/or shockwave source 120 and a center axis the axis of the X-ray system 290 by a system controller,

516: moving of the ultrasound and/or shockwave source 120 by means of a hexapod drive 180 to compensate (at least partially) for the displacement of axes and/or relative rotations,

518: taking a second image, the image showing the first X-ray absorbing object 127 and the second X-ray absorbing object 128,

520: processing of the second image, calculating the centers of and/or the distance between the first X-ray absorbing object 127 and the second X-ray absorbing object 128, and estimating the displacement (that may remain as a result of incomplete compensation at step 516, or that occurred anew) between the axis of the ultrasound and/or shockwave source 120 and the X-ray system 290 by a system controller,

522: checking whether the axes are aligned and there is no displacement or a displacement below a threshold between the images; If not aligned (N), go to 516, if yes (Y) go to 524
524: END Steps 516 to 522 may be repeated multiple times until the offset between the images may be within a predefined limit or further iterations do not reduce the offset.

Figure 5:
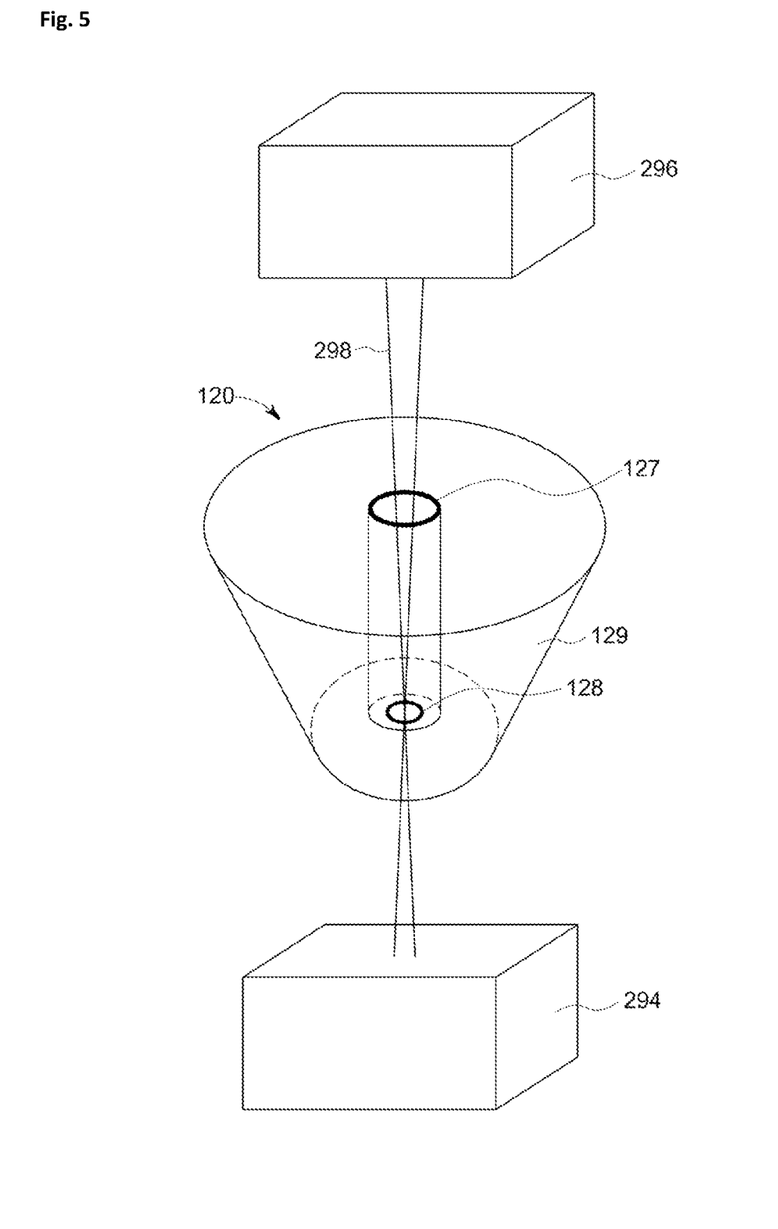
FIG. 5 shows a sketch of a focal phantom.

FIG. 5 shows a sketch of a focal phantom. An ultrasound and/or shockwave source 120 may have a first X-ray absorbing object 127 and a second X-ray absorbing object 128 distant in z-direction from each other. Both X-ray absorbing objects may be arranged symmetrical to the center axis of the source. Both X-ray absorbing objects may have different sizes and a symmetrical structure. They may be rings of different diameters. The first X-ray absorbing object 127 and a second X-ray absorbing object 128 may be removable from the ultrasound and/or shockwave source 120.

In this embodiment, a shock wave source having a centered cylindrical coil 122 within a reflector 129 is shown. The first X-ray absorbing object 127 may be at one end of the coil, where the second X-ray absorbing object 128 may be at the other side thereof. An X-ray beam 298 from X-ray tube 294 passes through the source 120 and produces images of the Y-ray absorbing objects at the detector. The axis of the ultrasound and/or shockwave source 120 may be moved by the hexapod drive 180 until the images of both X-ray absorbing objects are centered. In this case, the source 120 and the X-ray system 290 are on the same axis.

Figure 6:
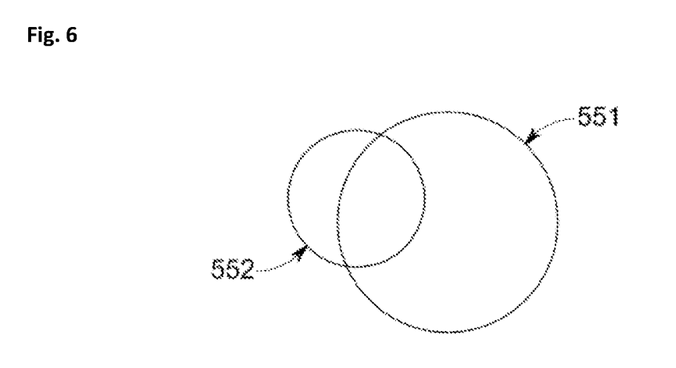
FIGS. 6, 7, and 8 show X-ray images made with the procedure steps.
Figure 7:
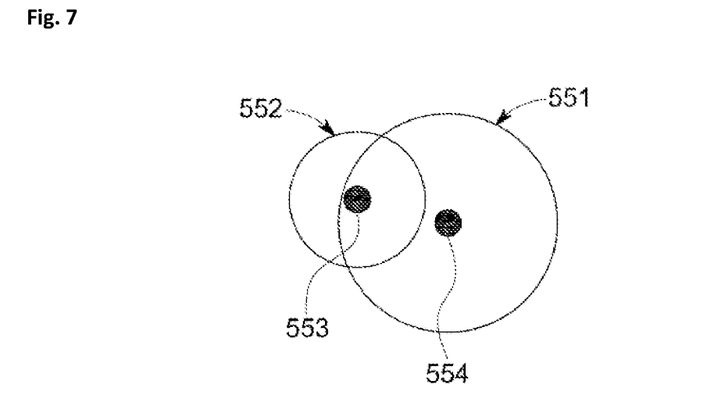
Figure 8:
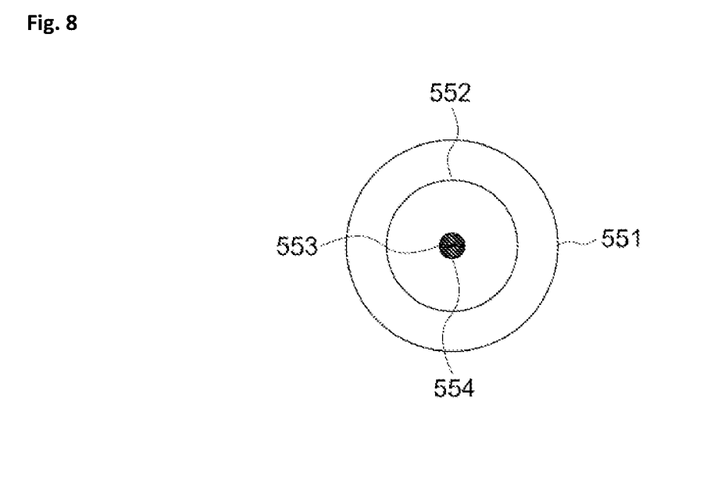

FIGS. 6 to 8 show X-ray images made with the procedure steps as explained in FIG. 4 with a focal phantom of FIG. 5. Here, FIG. 6 shows an X-ray image as made in step 512. It may show an X-ray image 551 of first X-ray absorbing object 127 and an X-ray image 552 of second X-ray absorbing object 128. If the axis of the X-ray system 290 is not aligned with the axis of the ultrasound and/or shockwave source.

120, the objects are not centered. In step 514 the center 554 of X-ray image of first X-ray absorbing object and the center 553 of X-ray image of second X-ray absorbing object are determined. FIG. 8 shows the image taken in step 518 with calculated centers from step 520, which overlap, as in this example the axis may be aligned. If the axes are still not aligned, then the centers would not be at the same position. In this case another iteration may be made.

Figure 9:
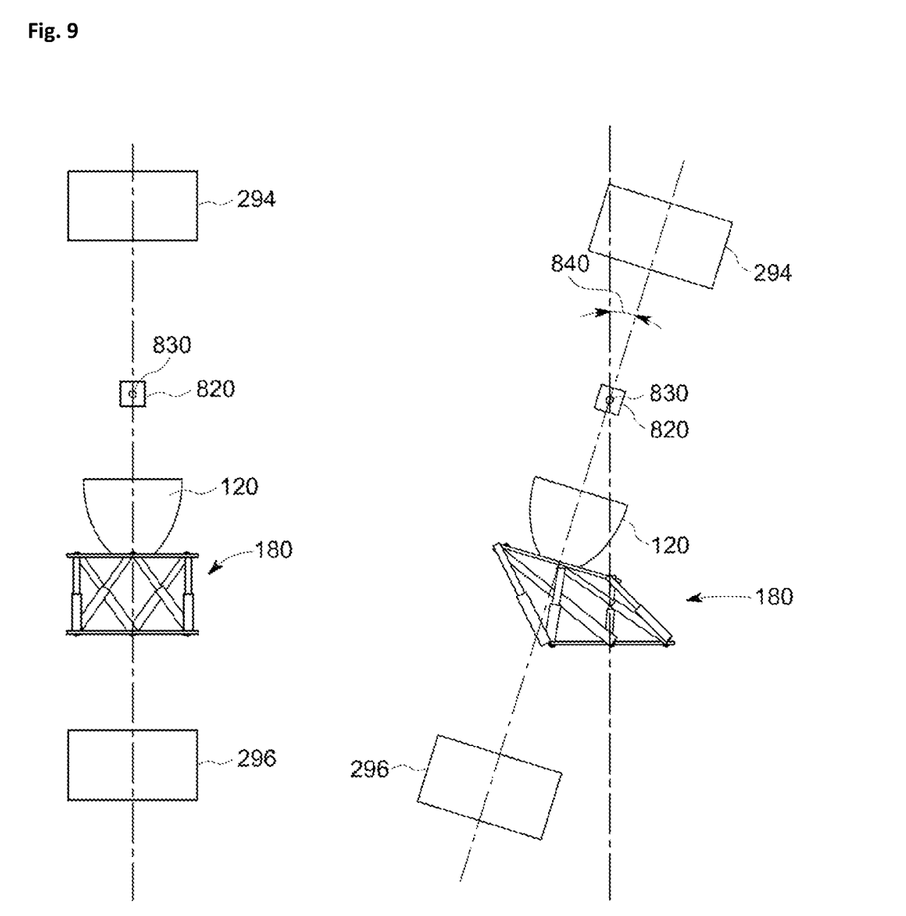
FIG. 9 shows an embodiment in two tilted positions.

FIG. 9 shows an embodiment in two tilted positions. At the left side, a shock wave and/or ultrasound therapy system is shown in vertical position. At the right side, the same system is shown in position tilted at an angle 840 around an axis 830 at the center of stone 820. Here the tilt axis is aligned with an axis of a stone. The image would look the same if the tilt axis is aligned with an axis of a known object or a phantom.

Figure 10:
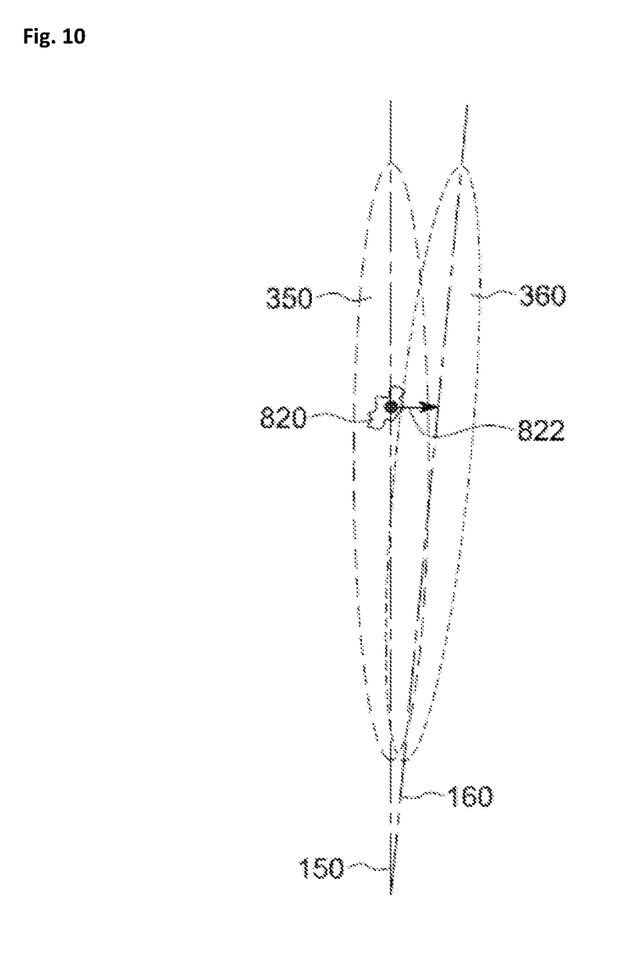
FIG. 10 shows focal volume positions with tilting.

FIG. 10 shows focal volume positions with tilting in a side view. On the left side, a first focal volume 350 is shown around the center axis 150 in a first state. When tilting the ultrasound and/or shockwave source about an angle, this focal volume is displaced to second focal volume 360 around a tilted center axis 160. In this figure, a tilt angle of approximately 4° is shown. It can be seen that the first focal volume from a normal state and the second focal volume from a tilted state together cover roughly twice the volume at the center of the focal volumes. A kidney stone 820, which may be centered to the center axis 150 in a first state, may move by respiration movement in a direction 822 to a second position, which then may be close to the tilted center axis 160. As the tilt of the ultrasound and/or shockwave source is synchronized with the respiration movement and therefore with the movement of the kidney 810 and with the movement of the kidney stone 820, the kidney stone is always approximately at the center axis of the ultrasound and/or shockwave source and therefore within the focal volume. This ensures a high energy coupling into the stone at any time.

Figure 11:
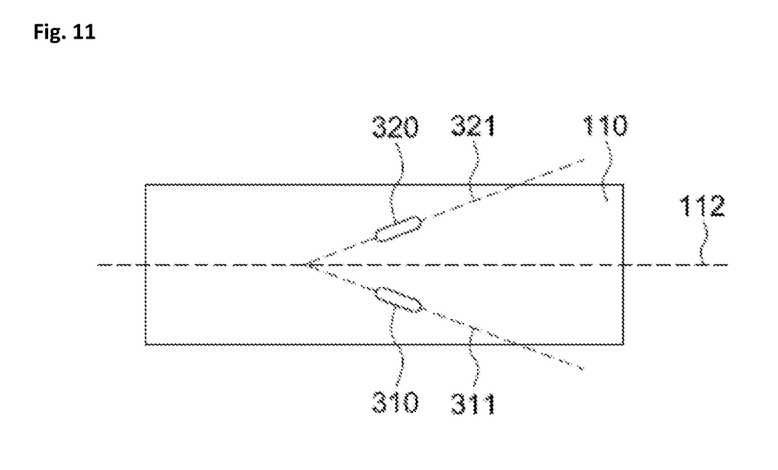
FIG. 11 shows a top view.

FIG. 11 shows a top view. As the kidneys not only move roughly parallel to the longitudinal axis 112 of the body and therefore of the patient table, but also move slightly sidewards, the ultrasound and/or shockwave source may be rotated around the center axis 150 in a first direction, such that the tilt results in movement in a first tilt direction 311 under an angle to the longitudinal axis 112. Alternatively, the ultrasound and/or shockwave source may be rotated into an opposing second position, resulting in a tilting movement in a second tilt direction 321. The focal volume covered during the tilt movement is indicated with reference number 310 for the first tilt direction 311 and with reference number 320 for the second tilt direction 321.

Figure 12:
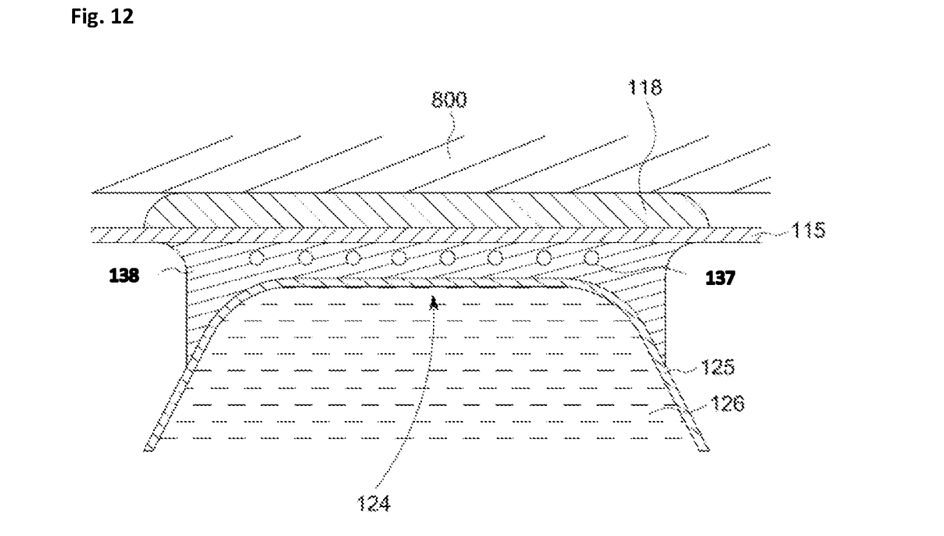
FIG. 12 shows a more detailed view of the coupling between ultrasound and/or shockwave source and patient.

FIG. 12 shows a more detailed view of the coupling between ultrasound and/or shockwave source and patient. A cushion 125 covers the interior of an ultrasound and/or shockwave source filled with a liquid 126 which may include water.

The cushion 125 may include an at least partially flexible polymer material and may have an exit section 124 through which ultrasound and/or shockwaves pass to the exterior. This exit section 124 may be directly coupled to a patient 800 or indirectly via a patient film 115 to the patient. There may be a layer of coupling gel 128, also known as ultrasound gel or acoustic gel at the top of the exit section 124 to allow coupling of the ultrasound and/or shock-wave energy. There may be another layer of coupling gel 118 or another immersion media, e.g., an ultrasound gel, water between the patient film 115 and the patient 800. There may be a plurality of small air bubbles 127 enclosed in the coupling gel 128.

Figure 13:
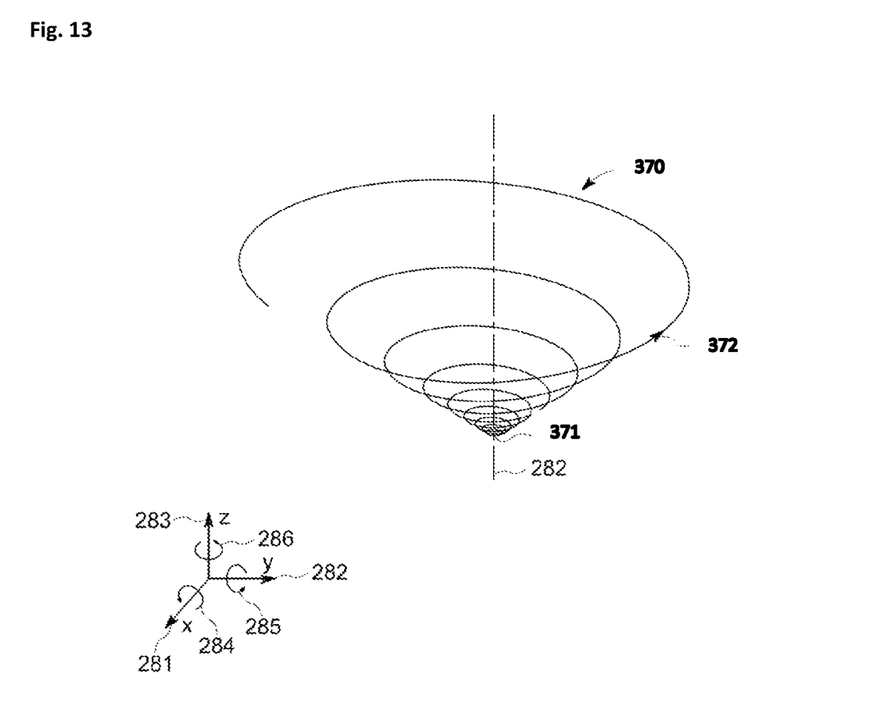
FIG. 13 shows a spiral movement pattern of the ultrasound and/or shockwave source.

FIG. 13 shows a spiral movement pattern of the ultrasound and/or shockwave source. There may be a spiral movement 370 in an X-Y plane combined with a translation in Z direction towards the patient film. The movement may start at a start point 371 centered close to the center axis 150 making circles with continuously increasing radius and moving at the same time towards the patient film as indicated by arrow 372. This movement may squish air bubbles in a radial direction out of the space between the cushion and the patient film. There may also be a spiral movement in a plane orthogonal to the center axis of the ultrasound and/or shockwave source combined with a translation in a direction of the center axis. This translation may be in a direction to a patient film and/or a patient. This may be slightly different to the previous movement, as the center axis of the ultrasound and/or shockwave source must not be aligned with the Z-axis.

As understood in related art, the term "and/or", as used in connection with a recitation involving an element A and an element B, covers embodiments having element A alone, element B alone, or elements A and B taken together.

It will be appreciated to those skilled in the art having the benefit of this disclosure that this invention is believed to provide a shock wave and/or ultrasound device. Further modifications and alternative embodiments of various aspects of the invention will be apparent to those skilled in the art in view of this description. Accordingly, this description is to be construed as illustrative only and is provided for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS 100 shock wave and/or ultrasound therapy system
110 patient table
112 longitudinal axis
115 patient film
120 ultrasound and/or shockwave source
122 coil
124 exit section of cushion
125 coupling cushion
126 water
127 first X-ray absorbing object
128 second X-ray absorbing object
129 reflector
130 shock wave generator
137 air bubbles
138 coupling gel
150 center axis
160 tilted center axis
170 base
180 hexapod drive
181-186 linear actuators
191-193 mounting positions at base
194-196 mounting positions at ultrasound and/or shockwave source
220 stand
240 positioning device
280 cartesian coordinate system
281 x-axis
282 y-axis
283 z-axis
284 tilt around the x-axis
285 tilt around the y-axis
286 tilt around the z-axis
290 X-ray system
292 C-arm
293 C-arm drive
294 X-ray detector
296 X-ray tube
298 X-ray beam
310 first focal volume coverage
311 first tilt direction
320 second focal volume coverage
321 second tilt direction
350 first focal volume
360 second focal volume
370 spiral movement
371 spiral start point
372 direction of spiral movement
400 control panel
410 system controller
420 hexapod control
430 C-arm control
510-524 Method steps
551 X-ray image of first X-ray absorbing object
552 X-ray image of second X-ray absorbing object
553 center of X-ray image of second X-ray absorbing object
554 center of X-ray image of first X-ray absorbing object
800 patient
810 kidney
820 kidney stone
822 movement of kidney stone
830 tilt axis
840 tilt angle

What is claimed is:

1. A device comprising:
a source configured to generate at least one of shockwaves and ultrasound, and
a base,
wherein the source is suspended on a hexapod drive, the hexapod drive including six linear actuators,
wherein the six linear actuators are attached in pairs to three mounting positions at the base and in pairs to three mounting positions at the source,
wherein:
a first end of every other linear actuator of the six linear actuators is attached to a different of the three mounting positions at the base, and
a second end of said every other linear actuator of the six linear actuators is attached to a different of the three mounting positions at the source.

2. The device according to claim 1, wherein each connection of a linear actuator to a component of the device includes a mechanical joint.

3. The device according to claim 1, wherein the hexapod drive is configured to provide a movement with at least five degrees of freedom including a displacement along three orthogonal axes and at least two degrees of tilt.

4. The device according to claim 1, wherein the device is arranged in a cartesian coordinate system with a y-axis being a longitudinal axis through a center of a patient table, an x-axis being orthogonal to the y-axis and in a plane of a surface of the patient table, and a z-axis being orthogonal to the plane of the surface of the patient table and orthogonal to the x-axis and the y-axis and in a direction upward from the patient table.

5. The device according to claim 1, wherein the source is configured to generate the shockwaves that propagate in a direction towards a patient table located above the source and that have a focal volume above the patient table.

6. The device according to claim 1, wherein the hexapod drive is coupled to a movement sensor and configured to effectuate a tilting movement as a function of a movement sensor signal from the movement sensor.

7. The device according to claim 6, wherein the movement sensor comprises at least one of a respiration sensor, a camera, and a heart pulse sensor.

8. The device according to claim 1, wherein the hexapod drive is configured to provide a first movement in a direction of a center axis of the source and concurrently a second movement to avoid and/or remove air bubbles at an exterior surface of a cushion covering the source.

9. The device according to claim 1, wherein the hexapod drive is configured to provide a spiral movement in a plane orthogonal to a center axis combined with a translation in a direction of the center axis.

10. The device according to claim 1,
wherein linear actuators of the six linear actuators include at least one of a hydraulic jack and a pneumatic jack and electric linear actuators.

* * * * *